United States Patent [19]

Byrne et al.

[11] Patent Number: 5,665,766

[45] Date of Patent: Sep. 9, 1997

[54] ESTER OF AN ORGANIC NITRATE AND A SALICYLATE

[75] Inventors: William Byrne, Dublin; Andrew Rynne, Clane, both of Ireland

[73] Assignee: Cal International Limited, Dublin, Ireland

[21] Appl. No.: 374,650

[22] PCT Filed: Jul. 26, 1993

[86] PCT No.: PCT/IE93/00040

§ 371 Date: Jan. 30, 1995

§ 102(e) Date: Jan. 30, 1995

[87] PCT Pub. No.: WO94/03421

PCT Pub. Date: Feb. 17, 1994

[30] Foreign Application Priority Data

Jul. 30, 1992 [IE] Ireland ................................. 92 2474

[51] Int. Cl.$^6$ ........................ A61K 31/34; C07D 493/00
[52] U.S. Cl. .......................... 514/470; 514/475; 514/533; 514/548; 549/464
[58] Field of Search .............................. 514/475, 533, 514/548, 470; 549/464

[56] References Cited

U.S. PATENT DOCUMENTS

| | | | |
|---|---|---|---|
| 4,318,921 | 3/1982 | Smith | 424/304 |
| 4,695,465 | 9/1987 | Kagasawa et al. | 424/449 |
| 4,769,379 | 9/1988 | Leitold et al. | 514/290 |
| 4,891,373 | 1/1990 | Stoss et al. | 514/470 |

FOREIGN PATENT DOCUMENTS

| | | |
|---|---|---|
| 0449426 | 10/1991 | European Pat. Off. |
| WO 92/01668 | 2/1992 | WIPO |
| WO 92/16506 | 10/1992 | WIPO |

OTHER PUBLICATIONS

European Heart Journal, vol. 12, Sup.A. 1991, pp. 2–4 "Why Use a Nitrate in 1990".

European Heart Journal, vol. 9, Supp.A 1988, pp. 45–49 "Mechanisms For The In Vivo Antiplatelet Effects of Isosorbide Dinitrate".

Eur. J. Clin. Pharmacology, vol. 25, 1983, pp. 779–782 "Pharmacological Internaction Between Nitroglycerin and Asprin After Acute and Chronic Aspirin Treatment of Healthy Subjects".

J. Cardiovascular Pharmacology, vol. 5, No. 5, 1983, pp. 874–877 "Influence of Aspirin on the Hemodynamic Effects of Sublingual Nitroglycerin".

AN 100 : 12587 Kim et al, "Phamaceutical Studies on the Estimation of Chloramphinzol with Antipyretics", Yahihak Hoech, 27(3), 207–13. *Abstract Only* 1983.

*Primary Examiner*—Marianne M. Cintins
*Assistant Examiner*—Keith MacMillan
*Attorney, Agent, or Firm*—Jacobson, Price, Holman & Stern, PLLC

[57] ABSTRACT

A pharmaceutical product for the relief of the symptoms of angina pectoris and the like comprises an ester of an organic nitrate and a salicylate or derivative thereof having antiplatelet activity.

25 Claims, 2 Drawing Sheets

ESTER OF AN ORGANIC NITRATE AND A SALICYLATE

This application is a 371 of PCT/IE93/00040, filed Jul. 26, 1993.

The invention relates to pharmaceutical products.

The term "organic nitrates" as used in this specification refers to pharmacologically active organic nitrate compounds which relieve, or act as prophylactic against, angina pectoris.

Organic nitrates are dilators of arterial and venous smooth muscle. The dilation action on the venous system increases the venous capacity allowing pooling of venous blood. This in turn reduces the volume of blood returning to the heart thereby lessening the strains on the heart muscle by reducing the pressure in the heart chambers (ventricles). This, in turn, reduces the oxygen requirements of the heart muscle. The dilation action on the arterial system is achieved by increasing the volume of the arterial system with consequent lower resistance to blood flow. This, in turn, reduces the work that the heart is required to do. In the coronary arteries (heart) a transient widening of the arteries (vasodilation) increases blood circulation to the heart muscle thereby increasing oxygen availability to the heart muscle.

Patients with coronary artery narrowing may suffer from angina pectoris which is usually brought on by exercise, emotion or eating. The organic nitrates by virtue of their action described above relieve the symptoms of angina pectoris.

In more detail, organic nitrates act in two ways—indirectly and directly.

Indirectly: they are smooth muscle relaxants and thus dilate both arterial and venous blood vessels. At lower doses their action is mainly on the venous system resulting in a decreased right and left ventricular filling pressure. At lower doses, however, they have little effect on the systemic (arterial) filling pressure. At higher doses, the arterial effects are more marked and decreased systemic resistance is accompanied by a reduction in blood pressure (Flaherty et al 1976). The renodilating and arterial effects of nitrates relieve ischaemia (the cause of angina, pain) by reducing determinates of myocardial oxygen demand.

Directly: they relieve ischaemia by direct action on the coronary vasculature thereby increasing intercoronary collateral flow and reversal of coronary artery spasm.

One widely used organic nitrate is isosorbide mononitrate (ISMN) which is an active metabolite of Isosorbide dinitrate (ISDN). ISMN has a high bioavailability and has a comparatively long half life (4–5 hours). Thus it is very suitable for prophylactic angina therapy. This is particularly so when it is presented as a sustained release formulation.

According to the invention there is provided a pharmaceutical product comprising a salicylate of an esterifiable organic nitrate.

The term "salicylate" refers to a salicylate or derivative or complex thereof having anti-platelet activity.

Preferably, the organic nitrate is directly esterifiable. In other words, the organic nitrate has an hydroxy group which is available for esterification.

The organic nitrate may be an isosorbide nitrate such as isosorbide 2-mononitrate or, most preferably isosorbide 5-mononitrate.

Alternatively, the organic nitrate is a glyceryl nitrate such as glyceryl trinitrate (also known as 1,2,3-Propanetriol trinitrate and Nitroglycerin).

Alternatively, the organic nitrate is a pentaerythritol nitrate such as pentaerythritol trinitrate (also known as Pentrinitrol).

Alternatively, the organic nitrate may be indirectly esterifiable by removal of a nitrate from the nitrate compound and replacement by an hydroxy group prior to esterification.

In this case, the organic nitrate may be selected from the group consisting of Erythritol Anhydride, Mannitol Hexanitrate, Trolnitrate Phosphate, Pentaerythritol Tetranitrate, Propatyl Nitrate, Clonitrate, and Isosorbide Dinitrate.

In a particularly preferred embodiment of the invention the product is formed by esterification of an esterifiable organic nitrate with acetylsalicylic acid.

The product may be adapted for oral administration or percutaneous administration.

The invention also provides a tablet or capsule comprising a pharmaceutical product of the invention.

The invention further provides a transdermal patch including a pharmaceutical product of the invention.

The invention especially preferably provides the compound Isosorbide 5-mononitrate-2-aspirinate.

In another aspect the invention provides a process for preparing a pharmaceutical product of the invention which comprises esterifying an esterifiable organic nitrate with acetylsalicylic acid.

Preferably, the esterification is carried out using a coupling reagent and/or a catalyst.

The coupling agent typically is a carbodiimide such as Dicyclohexylcarbodiimide (DCC).

The catalyst may comprise a pyridine derivative or paratoluene sulphonic acid.

Preferably, the esterification is carried out in non-aqueous conditions.

Typically, the process is carried out using methylenechloride as a solvent.

Preferably the process is carried out at a temperature below 5° C., most preferably at 0° C. or below.

The invention will be more clearly understood from the following description thereof given by way of example only.

EXAMPLE 1

Synthesis of acetylsalicyloxyisosorbide mononitrate

Materials:
Acetylsalicylic acid
Isosorbide mononitrate
Dicyclohexylurea (DCC)
Dimethylaminopyridine (DMAP)
Dichloromethane (dry)
Citric acid solution (20%w/v in water)
Sodium bicarbonate aqueous solution saturated
Sodium sulphate anhydrous Method:

Add DMAP (0.03 gm) and isosorbide mononitrate (1.85 gm,0.01M) to a cold (0° C.) and well stirred solution of acetylsalicylic acid (1.8 gm, 0.01M) in dry dichloromethane (10 ml). Gradually add DCC (2.06 gm, 0.01M). Stir for 10 minutes at room temperature. Remove the precipitate by filtration. The filtered solution was washed with 2×25 ml aliquots of cold 20% citric acid solution and then 2×25 ml aliquots of saturated sodium bicarbonate solution. Dry the lower organic layer with anhydrous sodium sulphate filter and remove the solvent in vacuo. The product is purified on a sigel column using dichloromethane as eluent. The yield of the oily semisolid product was 50–75%.

The product has the following structure:

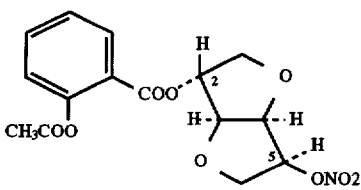

The product may be named as Isosorbide-5-mononitrate-2-aspirinate, or 2-{2-Acetoxybenzoyl}-isosorbide-5-mononitrate, or 2-Acetylsalicyloxy-1,4,3,6-dianhydro-D-glucitol-5-nitrate.

Oil/low melting point solid Molecular formula $C_{15}H_{15}O_9N$
Molecular weight 353

Figure 1:
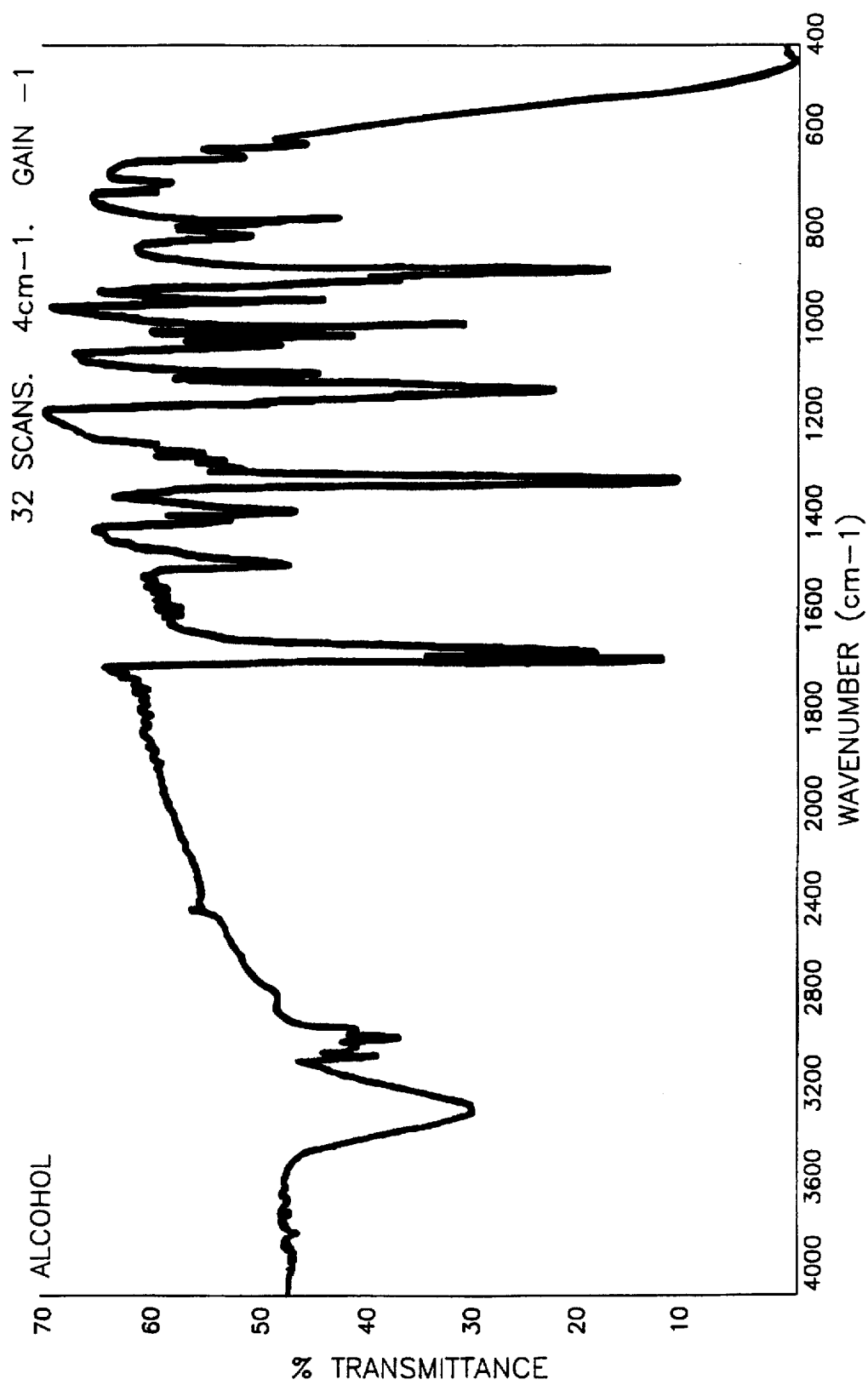
FIG. 1 shows infrared analysis for isosorbide monoitrate.
Figure 2:
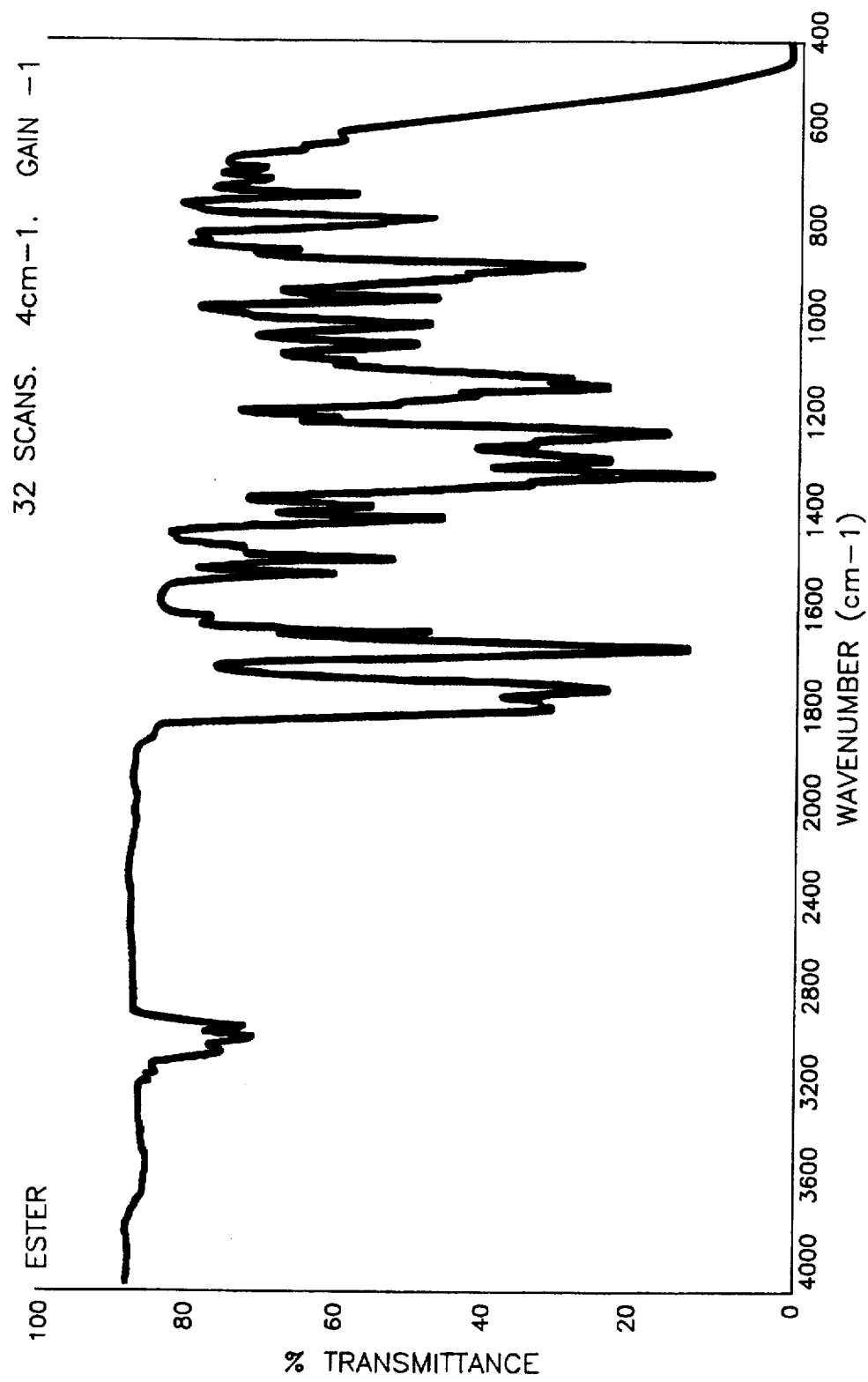
FIG. 2 shows infra red analysis for the product of the example.

Infra red spectrum (thin film) 1780,1740,1640 cm-1. The infra red analysis for isosorbide mononitrate is shown in FIG. 1. FIG. 2 is the infra red analysis for the product of the example.

Proton magnetic Resonance Spectrum See PMRBB-24 appended.

Thin Layer Chromatogram: Sigel GF 254/ dichloromethane rf=0.8.

Mass spectrum (EI) MI 353

Because of the inherent lability of the starter and product ester groupings it is necessary to select mild reaction conditions. The general method of Neises, B and Steglich, W, Angew. Chem. Int Ed Eng. 17 (1978) No. 7, 522–524 was selected because of the mild reacting condition. The direct formation of acetylsalicyloxyisosorbide-5-mononitrate from acetylsalicylic acid and isosorbide-5-mononitrate is accomplished by the use of the coupling reagent N,N-1-dicyclohexylcarbodiimide (DCC). The particular virtue of this method lies in its suitability for acid sensitive substrates such as esters. The rate of reaction is greatly increased by addition of catalytic amounts of 4-dimethylaminopyridine. Pyridine or p-toluene sulphonic acid may also be used.

Indirect Esterification

Acid chlorides react with primary and secondary alcohols to give esters in good yield.

Anhydrides may also be used for the esterification of alcohols in the presence of a suitable catalyst. Acidic catalysts such as sulphuric acid or zinc chloride and basic catalysts such as pyridine are generally used.

Direct Esterification

Direct esterification procedures involving carboxylic acids and alcohols can be accomplished by the addition of concentrated sulphuric acid or dry HCl to the reaction mixture.

Various methods for the preparation of esters are described in "Comprehensive Organic Transformations"—A guide to functional group preparations by Richard C. Larock, VCH Publishers Inc 1989, especially pages 966–972, 978–979, 980–981, 985–987, 989–990.

As the product of Example 1 is an oil/low melting point solid, it is likely to be particularly suitable for percutaneous application, by means of a transdermal patch or for oral application in the form of a capsule, such as a soft gelatin capsule.

A widely used organic nitrate is Isosorbide Mono or di nitrate. Such agents act directly on the coronary arteries dilating them and thus improving the blood flow to the heart muscle and thus relieving the pain of angina pectoris. Another way that organic nitrates in general relieve the pain of angina is by reducing the requirements of the myocardium (heart muscle) for oxygen by reducing the volume of blood returning to the heart.

The pharmaceutical products of the invention are particularly for the prophylaxis of chronic stable angina pectoris. The invention provides a new combined prophylactic therapy which will deal with the pain of angina and decrease the risk of thrombosis leading to heart attack. Patients with angina pectoris have diseased coronary arteries. All patients with this degree of diseased coronary arteries are at increased risk of developing thrombosis (or clot).

In a particularly preferred embodiment of the invention the anti-platelet agent is ASPIRIN (acetylsalicylic acid).

Aspirin has been widely used for many years as an analgesic/anti-pyretic and anti-inflammatory agent. As such, it is a most useful drug. In more recent years, however, it has been discovered that aspirin has a powerful anti-platelet effect. Platelets are microscopic particles within the blood that, under certain circumstances, can stick together to form a thrombus (clot). Aspirin prevents the sticking together of platelets and thus helps prevent the occurrence of heart attack or its complications.

The composition may be arranged for any desired release profile. The components may be released simultaneously or in some cases the organic nitrate is released more slowly than the Aspirin.

The effect of the pharmaceutical product of the invention is in the treatment of angina pectoris and in reducing the risk of developing myocardial infarction.

It is anticipated that, while the invention has been specifically described with reference to the combination of Isosorbide nitrate and Aspirin, it is expected that combination products of other known anti-angina agents are anti-platelet agents may also be used in combination.

Providing a nitrate and an anti platelet agent in a single dose pharmaceutical product has considerable advantages from a compliance viewpoint. If a patient is required to take a nitrate and aspirin separately there is a risk that one or other will be forgotten. It is also quicker and easier for a doctor to prescribe such a combination product.

The invention is not limited to the embodiments hereinbefore described which may be varied in detail.

We claim:

1. A salicylate ester of an organic nitrate, wherein said organic nitrate is either directly or indirectly esterifiable and selected from the group consisting of isosorbide nitrate, glyceryl nitrate, pentaerythritol nitrate, Mannitol Hexanitrate, Trolnitrate Phosphate, Pentaerythritol Tetranitrate, Propatyl Nitrate, Clonitrate and Isosorbide Dinitrate.

2. The salicylate ester as claimed in claim 1 wherein the isosorbide nitrate is isosorbide 5-mononitrate.

3. The salicylate ester as claimed in claim 1 wherein the isosorbide nitrate is isosorbide 2-mononitrate.

4. The salicylate ester as claimed in claim 1 wherein the glyceryl nitrate is glyceryl trinitrate.

5. The salicylate ester as claimed in claim 1 wherein the pentaerythritol nitrate is pentaerythritol trinitrate.

6. The salicylate ester as claimed in claim 1 wherein the product is formed by esterification of an esterifiable organic nitrate with an acetylsalicylic acid.

7. A process for preparing a salicylate ester which comprises esterifying an esterifiable organic nitrate with acetylsalicylic acid; wherein the salicylate ester of claim 1 is produced.

8. The process as claimed in claim 7 wherein the process is carried out in non-aqueous conditions.

9. The process as claimed in claim 7 wherein the process is carried out using methylene chloride as a solvent.

10. The process as claimed in claim 7 wherein the process is carried out at a temperature below 5° C.

11. The process as claimed in claim 7 wherein the process is carried out at a temperature 0° C. or below.

12. The process as claimed in claim 7 wherein the esterification is carried out using a coupling reagent.

13. The process as claimed in claim 12 wherein the coupling reagent is carbodiimide.

14. The process as claimed in claim 7 wherein the esterification is carried out using a catalyst.

15. The process as claimed in claim 14 wherein the catalyst is a pyridine derivative.

16. The process as claimed in claim 14 wherein the catalyst comprises a paratoluene sulfonic acid.

17. A pharmaceutical composition comprising, as an active ingredient, the salicylate ester as claimed in claim 1.

18. The pharmaceutical composition as claimed in claim 17 which is adapted for oral administration.

19. The pharmaceutical composition as claimed in claim 17 in the form of a tablet or capsule.

20. The pharmaceutical composition as claimed in claim 17 which is adapted for percutaneous administration.

21. The pharmaceutical composition as claimed in claim 17 in the form of transdermal patch.

22. Isosorbide 5-mononitrate-2-aspirinate.

23. A transdermal patch comprising isosorbide 5-mononitrate-2-aspirinate.

24. A soft capsule comprising isosorbide 5-mononitrate-2-aspirinate.

25. A method for the treatment of angina, comprising administering to a patient in need thereof, a pharmaceutical composition comprising an effective amount of a salicylate ester of an organic nitrate wherein said salicylate ester of an organic nitrate is selected from the group consisting of salicylate esters of isosorbide nitrate, glyceryl nitrate, pentaerythritol nitrate, Mannitol Hexanitrate, Trolnitrate Phosphate, Pentaerythritol Tetranitrate, Propatyl Nitrate, Clonitrate and Isosorbide Dinitrate.

* * * * *